United States Patent [19]

Crook et al.

[11] Patent Number: 5,002,731

[45] Date of Patent: Mar. 26, 1991

[54] CORROSION-AND-WEAR-RESISTANT COBALT-BASE ALLOY

[75] Inventors: Paul Crook; Aziz I. Asphahani, both of Kokomo; Steven J. Matthews, Greentown, all of Ind.

[73] Assignee: Haynes International, Inc., Kokomo, Ind.

[21] Appl. No.: 340,814

[22] Filed: Apr. 17, 1989

[51] Int. Cl.$^5$ .............................................. C22C 19/07
[52] U.S. Cl. .................................. 420/440; 148/425; 148/442; 420/436; 420/582; 420/585; 420/587; 420/588
[58] Field of Search ............... 420/440, 436, 582, 585, 420/587, 588; 148/408, 425, 419, 442

[56] References Cited

U.S. PATENT DOCUMENTS 3,865,585  2/1975  Rademacher .................... 420/440

Primary Examiner—R. Dean
Attorney, Agent, or Firm—Joseph J. Phillips

[57] ABSTRACT

Disclosed is a cobalt-base alloy that has a valuable combination of both corrosion- and wear-resistant properties. The alloy nominally contains, in percent by weight, 25.5 chromium, 8.5 nickel, 3.0 iron, 5 molybdenum, 2 tungsten, 0.40 silicon, 0.75 manganese, 0.06 carbon, 0.08 nitrogen and the balance cobalt plus normal impurities normally found in alloys of this class. The alloy may also contain copper and certain "carbide formers" (i.e., columbium, tantalum, titanium, vanadium and the like) to tie up excess carbon and/or nitrogen that may be present.

4 Claims, No Drawings

CORROSION-AND-WEAR-RESISTANT COBALT-BASE ALLOY

This invention relates to an alloy that is uniquely corrosion resistant and wear resistant and, more specifically, to a cobalt-base alloy containing critical contents of carbon and nitrogen.

BACKGROUND AND PRIOR ART

There are many distinctive industries within the metals art. Entire industries are based on various metallurgical products: high temperature resistant alloys (superalloys), corrosion-resistant alloys, wear-resistant alloys, and the like. These products are not readily interchangeable because each has a certain set of inherent properties that are not found in other products. For example, superalloys are strong at high temperature but are notoriously subject to wear. Corrosion-resistant alloys have excellent resistance to wet corrosion exposure but are generally subject to wear and are low in strength. Wear-resistant alloys are superior under erosion and wear conditions but are generally brittle and most of them do not offer appreciable corrosion resistance.

By way of composition, superalloys may be nickel and/or cobalt base; corrosion-resistant alloys are generally nickel base; and wear-resistant alloys are usually cobalt base.

Furthermore, the metallurgical structures of these alloys generally vary depending upon the required properties. Superalloys are known to have a strong solid solution matrix which may be dispersed with gamma prime. Corrosion-resistant alloys generally have a solid solution matrix and are free of precipitates, i.e., carbides. Wear-resistant alloys must depend upon a high content of precipitates, especially carbides, to provide the wear properties.

Much research has been directed toward the improvement of cobalt-base alloys. The pioneer invention of cobalt-base superalloys was disclosed by Elwood Haynes in U.S. Pat. No. 873,745 (Dec. 17, 1907) followed by his subsequent U.S. Pat. Nos. 1,057,423; 1,057,828; and 1,150,113. These alloys were generally used as cutting tools, utensils and the like implements. Later, cobalt-base alloys were modified by Austenal Laboratories under the now Howmedica trademark VITALLIUM® for use as cast dentures as taught in U.S. Pat. Nos. 1,958,446, 2,135,600, and 4,514,359 and also for use as components of gas turbine engines as taught in U.S. Pat. No. 2,381,459.

A wrought or cast cobalt-base alloy was disclosed in U.S. Pat. No. 2,704,250. The alloy known in the art as Alloy 25, has adequate corrosion resistance but has relatively poor wear (erosion) resistance. U.S. Pat. Nos. 3,865,585 and 3,728,495 disclose a nickel-free alloy with high nitrogen and carbon contents for use as dental prostheses articles. U.S. Pat. No. 2,486,576 relates to a novel heat-treating process for cobalt-base alloys. Disclosed are several cobalt chromium alloys containing manganese, nickel and molybdenum. U.S. Pat. No. 3,237,441 discloses a cobalt-base alloy for use as a tube rolling mill plug. The alloy has a high carbon content and is nitrogen free.

The Pfizer Hospital Products Group Inc. has recently made improvements in the VITALLIUM® alloys mentioned hereinabove. The alloys are made by an oxide dispersion process as disclosed in U.S. Pat. Nos. 4,714,468; 4,668,290, 4,631,290 corresponding to European Patent Application No. 0-195,513.

The patents mentioned above, of course, are only a small portion of the extensive research and development of cobalt-base alloys over the past 75 years. Each invention provided improvements in a limited number of engineering properties in strength, corrosion resistance and/or wear resistance. In the present industrial world, there is an urgent need for alloys with higher strength, capable of operating under more severe corrosive and wear conditions.

OBJECTS OF THIS INVENTION

In the present art, there is no single alloy that has the unique combination of all the diverse properties: strength, corrosion and wear resistance, as mentioned above.

Therefore, it is a principal object of this invention to provide an alloy with high strength and excellent corrosion and wear resistance.

It is another object of this invention to provide an alloy that is readily produced at a competitive cost.

It is still another object of this invention to provide an alloy that contains minimum contents of high cost strategic metals, i.e., columbium, tantalum and the like.

SUMMARY OF THE INVENTION

The above objects and other benefits of this invention that may be discerned by those skilled in the art are provided by the alloy described in Table 1.

Subsequent data herein will show that, within a specific range of Co—Cr—Mo—W alloys, a critical combination of carbon and nitrogen each effectively adjusted to provide an unexpected improvement in the art. The alloy of this invention is characterized by an enhanced corrosion resistance and also an enhanced resistance to cavitation erosion. These characteristics are normally not found in a single cobalt-base alloy in the present art.

DISCUSSION OF TESTING RESULTS

Pitting Tests

To evaluate their resistance to pitting, all the experimental alloys were immersed in Green Death (7v/o $H_2SO_4 + 3$ v/o $HCl + 1$ w/o $FeCl_3 + 1$ w/o $CuCl_2$), following ASTM G31 procedures. For comparative purposes alloys 6B 21 and 25 were also tested.

For each alloy, the critical pitting temperature (i.e., the lowest temperature at which pitting occurs within a 24 hour test period) was determined by running tests st several temperatures. To attain temperatures above boiling point, an autoclave was used. Two samples of each alloy were tested at each temperature.

After test, the samples were examined using a binocular microscope. The presence of even one pit on one sample was considered a negative result

Stress Corrosion Cracking Tests

The susceptibility of the experimental alloys and of alloys 6B, 21 and 25 to stress corrosion cracking was determined by testing in boiling solution of 30% magnesium chloride, according to the procedures described in ASTM Standard G30. The two stage method of stressing the U-bend sample was used, all samples being prepared from 0.125 inch thick annealed material.

Three samples of each material were tested in each of the two media, and inspection of the samples was at specific time intervals (1, 6, 24, 168, 336, 504, 672, 840, and 1008 hours).

Cavitation Erosion Tests

To determine the resistance to cavitation erosion of the materials, the vibratory cavitation erosion test described in ASTM Standard G32 was utilized. Essentially, the test apparatus comprises a transducer (the source of the vibrations), a tapered cylinderical member, to amplify the oscillations, and a temperature controlled container, in which the test liquid is held.

The specimens, which were prepared from annealed plate of thickness 0.75 inch were shaped as cylindrical buttons of diameter 14.0 mm, with a 6.4 mm threaded shank, and were screwed into a threaded hold in the end of the tapered cylinder for test purposes. Some samples were tested for 48 hours, and others for 96 hours, in distilled water (maintained at a temperature of 60° F.) at a frequency of 20 KHZ and an amplitude of 2 mils, a measure of the weight loss being taken at intervals of 24 hours. By measuring the density of the test materials independently, a mean depth of erosion was calculated. Two samples of each alloy were tested.

The alloys of this invention were tested together with commercially known cobalt alloys as described in Table 2. For about 80 years Elwood Haynes' Alloy 6B has been the well-known cobalt-base alloy with outstanding wear-resistant properties and relatively low corrosion resistance. Alloys No. 21 and 25, marketed by Haynes International, Inc. under their registered trademark HAYNES ®, are well-known cobalt-base alloys with fairly good corrosion resistance or relatively low wear resistance. The nickel-base C-22 alloy, marketed by Haynes International, Inc. under their trademark HASTELLOY ®, is especially known for its resistance to pitting.

Table 3 presents the compositions of seven experimental alloys that were prepared for testing together with the known alloys described in Table 2.

The test specimens for the various testing were prepared in a fairly routine manner for alloys of this class. The alloys were melted as fifty-pound heats by the vacuum induction process, then electroslag remelted (ESR). The ESR products were forged, then hot rolled at 2200° F. into ¾ inch plate and finally solution annealed. One half of the annealed ¾ inch plate was further hot rolled at 2200° F. into ⅛ inch sheet and then solution annealed. The cavitation erosion test was made with the ¾ inch plate and all other testing was made with the ⅛ inch sheet.

The ease of melting, casting and processing the experimental alloys clearly suggests the alloys of this invention may be readily made in the form of castings, wrought products (sheet, tubing, wire, etc.), powder metal (sintering, spraying, et.), welding materials and the like.

The compositions in Table 1 contain cobalt plus impurities as balance. In the production of cobalt alloys of this class, impurities from many sources are found in the final product. These so-called "impurities" are not necessarily always harmful and some may actually be beneficial or have an innocuous effect.

Some of the "impurities" may be present as residual elements resulting from certain processing steps, or be adventitiously present in the charge materials, or they may be deliberately added for benefits known in the art; for example, calcium, magnesium, vanadium, titanium, aluminum, zirconium, manganese, rare earth metals such as cerium, lanthanum, yttrium and the like.

As is known in the art, certain elements, (vanadium, columbium, tantalum, hafnium, titanium and the like) may be present up to eight percent and preferably less than five percent in total content as so called "carbide formers" to tie-up carbon and/or nitrogen that may be present in excessive contents in the melt.

It is well-known in the art that molybdenum and tungsten are interchangeable in many alloy systems. In the alloy of this invention, these elements may be interchanged but only in part. Because of the economic advantages and the fact that it was found to be more effective in imparting to alloys of this type resistance to reducing acids, molybdenum is preferred. Thus, molybdenum must be present in the alloy of this invention at not less than 3% for optimum economic and technical benefits. It is well known in the art that a composition adjustment must be made because of the difference in the atomic weights of these elements, defined as about Mo=½ W. For example, to obtain the equivalent of 6.0 molybdenum, it is necessary to have 5% molybdenum and 2.0 tungsten. Because of the possible interchange, molybdenum plus tungsten may total up to 15% in the alloy of this invention. It is generally found in this art that, for whatever reasons, molybdenum is preferred in nickel alloys and tungsten is preferred in cobalt alloys. The cobalt alloy of this invention in contradistinction, requires molybdenum to be preferred and dominant over tungsten.

Boron may be present in the alloy of this invention in a small but effective trace content as low as about 0.001% and up to about 0.015% to obtain certain benefits as is known in the art.

Nickel must be present in the alloy of this invention to provide a valuable combination of desirable engineering characteristics. Mechanical, physical, and processing properties are improved. The nickel content may be varied from about 4 to about 16% dependent upon the requirements of certain specific uses. For example, nickel contents about 7 to 10% and preferably about 8.5% yield alloys that have outstanding corrosion and wear properties together with resistance to cavitation erosion, "Green Death" pitting, and also resistant to fusion zone cracking. As test data herein will show, this is an eminently unexpected combination of properties. The art usually finds that, in general, these properties are often mutually exclusive.

At the heart of this invention is the discovery that, within certain ranges, a combination of carbon and nitrogen enhances considerably the corrosion resistance of Co—Cr—Mo alloys, and that the resistance to cavitation erosion of these carbon and nitrogen-containing materials approximately equals that of a cobalt alloy containing an abundance of carbide precipitates.

In the course of this discovery, several experimental alloys of varying carbon and nitrogen contents were melted, processed into wrought sheet and plate, and tested. These alloys are listed in Table 3. In alloy 46, carbon and nitrogen were kept as low as possible. In alloys 48 and 49, these two elements were increased independently, to levels believed to be close to the solubility limits (additions beyond these limits, it was thought, would cause considerable precipitation, which would be deleterious in a corrosion sense). Finally, in alloys 89, 90 and 91, carbon and nitrogen were added in combination at levels which would facilitate processing (having found that nitrogen at 0.19 wt. % causes cracking problems during processing) and limit sensitization during welding. Alloy 92 contains excessive nitrogen plus carbon.

The well-known cobalt alloys 6B, 21, and 25 were also tested for comparison.

Study of Tables 4 and 5 reveals the extent of the improvement in corrosion resistance brought about by a combination of carbon and nitrogen. With regard to resistance to stress corrosion cracking (Table 4), an improvement with increasing carbon content within the soluble range was anticipated, since it is known to stabilize the face centered cubic form of cobalt and, in turn, would be expected to increase stacking fault energy, hence resistance to transgranular stress corrosion cracking failure. The role of carbon was found to be more complex, however, since the early failure of alloy 46 (low carbon and nitrogen) was intergranular in nature. Unexpected also were the positive influence of nitrogen and the powerful influence of carbon and nitrogen in combination (a combined carbon and nitrogen level of 0.19 wt. % being much more effective than a nitrogen content of 0.19 wt. % with low carbon). Thus the gist of the invention lies in the criticality of both carbon and nitrogen present in substantially equal contents.

With regard to pitting resistance, some improvement with increasing nitrogen content could have been anticipated, based on work with Ni—Cr—Mo—W alloys. The positive influence of carbon within this alloy system and the beneficial effects of carbon and nitrogen in combination were unanticipated, however.

Prior information concerning cavitation erosion of the cobalt-based alloys suggests that within the soluble range carbon should be deleterious due to its influence on stacking fault energy (the requirements for cavitation erosion resistance being opposite to those for resistance to stress corrosion cracking in a microstructural sense). Beyond the soluble range, carbon is known to be beneficial up to about 0.25 wt. % and then relatively innocuous in the approximate range 0.25 to 1.4 wt. %. The effects of nitrogen were previously unknown.

As is evident from Table 6, an unexpected positive influence of carbon upon cavitation erosion resistance was encountered during this discovery (comparing alloys 46 and 48). Furthermore, the resistance of 48 (containing 0.06 wt. % carbon) is approximately equal to that of alloy 6B (containing about 1.1 wt. % carbon). The positive influence of nitrogen, alone, and in combination with carbon, was also unanticipated.

Comparing the test results for alloys 89 and 90, it may be ascertained that nickel, also a known stabilizer of the face centered cubic form of cobalt, does not have a powerful influence on wear properties in the range 5.3 to 9.8 wt. %.

With regard to the standard cobalt alloys used for comparison, the compositions of which are given in Table 2, it is evident that alloys 6B and 21, although very resistant to cavitation erosion, possess much poorer corrosion resistance than the alloys of this invention. Conversely, alloy 25 possesses good corrosion properties but inferior resistance to cavitation erosion. Only in the alloys of this invention are good resistance to both corrosion and cavitation erosion found in combination.

Wet corrosion tests were made on selected alloys as disclosed in Table 8. The testing was conducted by ASTM G31 standard testing practices. The results show the wet corrosion resistance of the alloys of this invention are generally clearly superior over the prior art alloys, except for C-22 TM alloy. However, C-22 alloy does not have adequate cavitation erosion resistance. Alloy 92 has good corrosion resistance but, here also, the alloy has inadequate cavitation erosion resistance. Note the corrosion resistance to boiling acids of the alloys of this invention is superior over the cobalt-base alloy 25 which does not have the features of this invention.

It will be apparent to those skilled in the art that the novel principles of the invention disclosed herein, in connection with specific examples thereof, will support various other modifications and applications of the same. It is accordingly desired that, in construing the breadth of the appended claims, they shall not be limited to the specific examples of the invention described herein.

TABLE 1

ALLOY OF THIS INVENTION
Composition in Weight Percent

|  | Broad | Preferred Range | Preferred Alloy |
| --- | --- | --- | --- |
| Chromium | 22.0–30.0 | 24.0–27.0 | 25.5 |
| Nickel | 4.0–16.0 | 7.0–10.0 | 8.5 |
| Iron | Up to 7 | 2.0–4.0 | 3.0 |
| Ni + Fe | Up to 20 | 9.0–14.0 | 11.5 |
| Molybdenum* | 3.0–10.0 | 4.5–5.5 | 5.0 |
| Tungsten | Up to 5.0 | 1.5–2.5 | 2.0 |
| Silicon | 0.05–2.0 | 0.30–0.50 | 0.40 |
| Manganese | 0.05–2.0 | 0.50–1.00 | 0.75 |
| Carbon | 0.02–0.11 | 0.04–0.08 | 0.06 |
| Nitrogen | 0.03–0.12 | 0.06–0.10 | 0.08 |
| C + N | 0.06–0.20 | 0.10–0.18 | 0.14 |
| Copper | Up to 3 | Up to 3 | — |
| "Carbide Formers" | Up to 8 | Up to 5 | — |
| Cobalt Plus Impurities | Balance | Balance | Balance |

*Molybdenum must always exceed tungsten.

TABLE 2

PRIOR ART ALLOYS
Composition, Percent by Weight

| Alloy No. | 6B | 21 | 25 | C-22 |
| --- | --- | --- | --- | --- |
| Chromium | 30.0 | 27.9 | 20.0 | 22 |
| Nickel | 2.5 | 3.1 | 10.0 | Bal |
| Iron | — | 0.3 | 2.3 | 3 |
| Molybdenum | 1.0 | 5.4 | — | 13 |
| Tungsten | 4.0 | 0.1* | 14.8 | 3 |
| Silicon | 0.7 | 0.8 | 0.2 | — |
| Manganese | 1.4 | 0.8 | 1.5 | — |
| Carbon | 1.1 | 0.24 | 0.11 | — |
| Nitrogen | — | 0.007 | — | — |
| Cobalt Plus Impurities | Bal | Bal | Bal | — |

* = Less than

TABLE 3

EXPERIMENTAL ALLOY COMPOSITIONS
Percent by Weight

| Alloy No. | 46 | 48 | 49 | 89 | 90 | 91 | 92 |
| --- | --- | --- | --- | --- | --- | --- | --- |
| Chromium | 25.7 | 25.4 | 25.1 | 25.5 | 25.4 | 25.4 | 25.9 |
| Nickel | 5.4 | 5.4 | 6.1 | 5.3 | 9.8 | 9.6 | 14.7 |
| Iron | 2.1 | 2.1 | 1.8 | 3.0 | 3.2 | 2.9 | 3.0 |
| Molybdenum | 4.9 | 4.9 | 5.0 | 5.0 | 5.0 | 4.8 | 5.0 |
| Tungsten | 1.4 | 1.5 | 1.5 | 2.0 | 2.0 | 2.0 | 1.9 |
| Silicon | 0.1 | 0.1 | 0.2 | 0.4 | 0.4 | 0.4 | 0.4 |
| Manganese | 0.2 | 0.2 | 0.2 | 0.8 | 0.8 | 0.8 | 0.8 |
| Carbon | 0.004 | 0.06 | 0.005 | 0.09 | 0.07 | 0.07 | 0.08 |
| Nitrogen | 0.002* | 0.006 | 0.19 | 0.10 | 0.10 | 0.06 | 0.13 |
| Cobalt Plus Impurities | Bal | Bal | Bal | Bal | Bal | Bal | Bal |

* = Less than
Alloys 89, 90 and 91 are alloys of this invention.

TABLE 4

STRESS CORROSION CRACKING DATA
30% Magnesium Chloride at 118° C.

| Alloy | Time to Failure |
|---|---|
| 46 | 1 |
| 48 | 72 |
| 49 | 336 |
| 89 | 1008* |
| 90 | 1008* |
| 6B** | — |
| 21 | 24 |
| 25 | 1008* |

\* = No Cracking
\*\* = Unable to Bend into U-Shape

TABLE 5

PITTING TEST DATA
24 Hr. Period

Media: 7 v/o $H_2SO_4$ + 3 v/o HCl + 1 w/o $FeCl_3$ + 1 w/o $CuCl_2$

| Alloy | Pitting Temperature (Degree C.) |
|---|---|
| 46 | 110 |
| 48 | 120 |
| 49 | 115 |
| 89 | 130 |
| 90 | 125 |
| 6B | 45 |
| 21 | 85 |
| 25 | 110 |

TABLE 6

CAVITATION EROSION TEST DATA

| Alloy | Mean Depth at 48 Hr, MM |
|---|---|
| 46 | 0.0429 |
| 48 | 0.0231 |
| 49 | 0.0266 |
| 89 | 0.0186 |
| 90 | 0.0242 |
| 6B | 0.0236 |
| 21 | 0.0169 |
| 25 | 0.0536 |

TABLE 7

CAVITATION EROSION TEST RESULTS

| Alloy | Mean Depth of Erosion - MM | | | |
|---|---|---|---|---|
| | 24 Hr. | 48 Hr. | 72 Hr. | 96 Hr. |
| 89* | 0.0048 | 0.0186 | 0.0332 | 0.0495 |
| 90* | 0.0067 | 0.0242 | 0.0412 | 0.0605 |
| 91* | 0.0068 | 0.0234 | 0.0410 | 0.0582 |
| 92 | 0.0153 | 0.0392 | 0.0625 | 0.0877 |
| 25 | 0.0244 | 0.0536 | 0.0856 | 0.1151 |
| 6B | 0.0084 | 0.0236 | 0.0361 | 0.0495 |
| C = 22 | 0.1122 | 0.1935 | 0.2499 | 0.2965 |

\*Alloys of this invention

TABLE 8

WET CORROSION TESTING OF SELECTED ALLOYS

| Alloy | Corrosion Rates (Mils per Year) | | | |
|---|---|---|---|---|
| | Boiling 1% HCl | Boiling 2% HCl | Boiling 10% $H_2SO_4$ | Boiling 65% $HNO_3$ |
| 89 | 1.0 | 353.5 | 60.0 | 8.3 |
| 90 | 5.2 | 592.0 | 60.6 | 8.4 |
| 91 | 4.6 | 454.0 | 55.4 | 9.2 |
| 92 | 0.1 | 636.0 | 65.0 | 8.1 |
| 25 | 225.5 | 2431.5 | 130.5 | 30.8 |
| 6B | 169.5 | 5668.0 | 307.5 | 5433.0 |
| C-22 | 3.0 | 61.0 | 11.0 | 53.0 |

What is claimed is:

1. An alloy consisting essentially of, in weight percent, 22 to 30 chromium, 4 to 16 nickel, up to 7 iron, up to 20 Ni+Fe, 3 to 10 molybdenum, up to 5.0 tungsten, 0.05 to 2.0 silicon, 0.05 to 2.0 manganese, 0.02 to 0.11 carbon, 0.03 to 0.12 nitrogen, 0.06 to 0.20 C+N, copper up to 3.0, elements in the group known as carbide formers up to 8 and the balance cobalt plus impurities wherein the molybdenum exceeds the tungsten content and the carbon and nitrogen contents are in effective amounts to provide the combination of corrosion and wear properties.

2. The alloy of claim 1 containing 24 to 27 chromium, 7 to 10 nickel, 2 to 4 iron, 9 to 14 Ni+Fe, 4.5 to 5.5 molybdenum, 1.5 to 2.5 tungsten, 0.30 to 0.5 silicon, 0.50 to 1.0 manganese, 0.04 to 0.08 carbon, 0.06 to 0.10 nitrogen, and 0.10 to 0.18 C+N.

3. The alloy of claim 1 containing about 25.5 chromium, about 8.5 nickel, about 3.0 iron, about 5.0 molybdenum, about 2.0 tungsten, about 0.4 silicon, about 0.75 manganese, about 0.06 carbon, and about 0.08 nitrogen.

4. The alloy of claim 1 in the form of cast, wrought or powder products.

* * * * *